US010098909B2

(12) United States Patent
Tan et al.

(10) Patent No.: US 10,098,909 B2
(45) Date of Patent: Oct. 16, 2018

(54) IONIC COCRYSTAL OF LITHIUM, LISPRO, FOR THE TREATMENT OF FRAGILE X SYNDROME

(71) Applicants: Jun Tan, Tampa, FL (US); Roland Douglas Shytle, Largo, FL (US)

(72) Inventors: Jun Tan, Tampa, FL (US); Roland Douglas Shytle, Largo, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 15/425,367

(22) Filed: Feb. 6, 2017

(65) Prior Publication Data

US 2017/0224724 A1 Aug. 10, 2017

Related U.S. Application Data

(60) Provisional application No. 62/291,941, filed on Feb. 5, 2016.

(51) Int. Cl.
  *A61K 33/00* (2006.01)
  *A61K 31/60* (2006.01)
  *A61K 31/401* (2006.01)

(52) U.S. Cl.
  CPC ............ *A61K 33/00* (2013.01); *A61K 31/401* (2013.01); *A61K 31/60* (2013.01)

(58) Field of Classification Search
  CPC ....... A61K 33/00; A61K 31/60; A61K 31/401
  USPC ....................................................... 424/722
  See application file for complete search history.

(56) References Cited

U.S. PATENT DOCUMENTS 3,773,919 A 11/1973 Boswell et al.

FOREIGN PATENT DOCUMENTS

EP 0058481 A1 8/1982
EP 0133988 A2 3/1985

OTHER PUBLICATIONS

Zhonghua Liu; title: Lithium: A Promising Treatment for Fragile X Syndrome; ACS Chem Neurosci. Jun. 18, 2014; 5(6): 477-483, Published online May 11, 2014.*
Author: Adam J. Smith, et al.; title: Improving Lithium Therapeutics by Crystal Engineering of Novel Ionic Cocrystals; Mol. Pharmaceutics, 2013, 10 (12), pp. 4728-4738, Publication Date (Web): Nov. 5, 2013.*
Bear, M.F. et al., The mGluR theory of fragile X mental retardation, *TRENDS* in Neurosciences, Jul. 2004, 27(7):370-377, 2004 Elsevier Ltd.
Koukoui, S.D. et al., Neuroanatomical, molecular genetic, and behavioral correlates of fragile X syndrome, Brain Research Reviews, Jul. 17, 2006, 53:27-38, 2006 Elsevier B.V.
Crawford, D.C. et al., Fragile X CGG repeat structures among African-Americans: identification of a novel factor responsible for repeat instability, *Human Molecular Genetics*, May 11, 2000, 9(12):1759-1769, 2000 Oxford University Press.
Garber, K.B. et al., Fragile X syndrome, European Journal of Human Genetics, Feb. 20, 2008, 16:666-672, 2008 Nature Publishing Group.
Crawford, D.C. et al., FMR1 and the Fragile X Syndrome: Human Genome Epidemiology Review, *Genet Med*, 2001, 3(5):1-27.
Belmonte, M.K. et al., Fragile X syndrome and autism at the intersection of genetic and neural networks, Nature Neuroscience, Oct. 2006, 9(10):1221-1225, 2006 Nature Publishing Group.
Hagerman, R.J. et al., Recent advances in fragile X: a model for autism and neurodegeneration, Current Opinion in Psychiatry, 2005, 18:490-496, 2005 Lippincott Williams & Wilkins.
Hatton, D.D. et al., Autistic Behavior in Children With Fragile X Syndrome: Prevalence, Stability, and the Impact of FMRP, American Journal of Medical Genetics Part A, Mar. 27, 2006, 140A:1804-1813, 2006 Wiley-Liss, Inc.
Kau, A.S.M. et al., Social Behavior Profile in Young Males With Fragile X Syndrome: Characteristics and Specificity, American Journal of Medical Genetics, 2004, 126A:9-17, 2004 Wiley-Liss, Inc.
Loesch, D.Z. et al., Molecular and cognitive predictors of the continuum of autistic behaviours in fragile X, *Neurosci Biobehav Rev*, 2007, 31(3):1-21.
Moy, S.S. et al., Advances in behavioral genetics: mouse models of autism, Molecular Psychiatry, 2008, 13:4-26, 2008 Nature Publishing Group.
Sullivan, K. et al., ADHD Symptoms in Children With FXS, American Journal of Medical Genetics Part A, Jun. 8, 2006, 140A:2275-2288, 2006 Wiley-Liss, Inc.
Doble, B.W. et al., GSK-3: tricks of the trade for a multi-tasking kinase, *J Cell Sci*, Apr. 1, 2003, 116(Pt 7):1-26.
Jope, R.S. et al., The glamour and gloom of glycogen synthase kinase-3 (GSK$_3$), *TRENDS* in Biochemical Sciences, Feb. 2004, 29(2):95-102, 2003 Elsevier Ltd.
Mines, M.A. et al., Glycogen synthase kinase-3: a promising therapeutic target for fragile X syndrome, Frontiers in Molecular Neuroscience, Nov. 1, 2011, 4(35):1-8.
Mines, M.A. et al., GSK3 Influences Social Preference and Anxiety-Related Behaviors during Social Interaction in a Mouse Model of Fragile X Syndrome and Autism, PLOS One, Mar. 16, 2010, 5(3):1-12, 2010 Mines et al.
Klein, P.S. et al., A molecular mechanism for the effect of lithium on development, *Proc. Natl. Acad. Sci. USA*, Aug. 1996, 93:8455-8459.

(Continued)

*Primary Examiner* — Yanzhi Zhang
(74) *Attorney, Agent, or Firm* — Saliwanchik, Lloyd & Eisenschenk

(57) ABSTRACT

The invention relates to a pharmaceutical composition comprising an ionic co-crystal (ICC) of lithium with salicylic acid and 1-proline (LISPRO). The pharmaceutical composition can further comprise an anti-inflammatory agent, for example, salicylic acid. An embodiment of the invention provides a method for treating Fragile X Syndrome (FXS) in a subject by administering to the subject a composition comprising a pharmaceutically effective amount of LISPRO.

12 Claims, 6 Drawing Sheets

(56) References Cited

OTHER PUBLICATIONS

Min, W.W. et al., Elevated glycogen synthase kinase-3 activity in Fragile X mice: Key metabolic regulator with evidence for treatment potential, *Neuropharmacology*, Feb. 2009, 56(2):1-26, 2008 Elsevier Ltd.

Yuskaitis, C.J. et al., Evidence of reactive astrocytes but not peripheral immune system activation in a mouse model of Fragile X syndrome, Biochimica et Biophysica Acta, Jun. 23, 2010, 1802:1006-1012, 2010 Elsevier B.V.

Yuskaitis, C.J. et al., Glycogen Synthase Kinase-3 Regulates Microglial Migration, Inflammation, and Inflammation-Induced Neurotoxicity, *Cell Signal*, Feb. 2009, 21(2):1-21.

Yuskaitis, C.J. et al., Lithium ameliorates altered glycogen synthase kinase-3 and behavior in a mouse model of Fragile X syndrome, *Biochem Pharmacol*, Feb. 15, 2010, 79(4):1-21.

Liu, Z-H. et al., Dissociation of social and nonsocial anxiety in a mouse model of fragile X syndrome, *Neurosci Lett*, Apr. 17, 2009, 454(1):1-9.

Liu, Z-H. et al., Lithium ameliorates phenotypic deficits in a mouse model of fragile X syndrome, *International Journal of Neuropsychopharmacology*, 2011, 14:618-630, CINP 2010.

Liu, Z-H. et al., Lithium reverses increased rates of cerebral protein synthesis in a mouse model of fragile X syndrome, *Neurobiol Dis*, Mar. 2012, 45(3):1-22.

Berry-Kravis, E. et al., Open-Label Treatment Trial of Lithium to Target the Underlying Defect in Fragile X Syndrome, *J Dev Behav Pediatr*, Aug. 2008, 29(4):293-302, 2008 Lippincott Williams & Wilkins.

Comery, T.A. et al., Abnormal dendritic spines in fragile X knockout mice: Maturation and pruning deficits, *Proc. Natl. Acad. Sci. USA*, May 1997, 94:5401-5404, 1997 The National Academy of Sciences of the USA.

Waterhouse, E.G. et al., New insights into the Role of Brain-derived Neurotrophic Factor in Synaptic Plasticity, *Mol Cell Neurosci*, Oct. 2009, 42(2):1-20.

Lauterborn, J.C. et al., Brain-Derived Neurotrophic Factor Rescues Synaptic Plasticity in a Mouse Model of Fragile X Syndrome, The Journal of Neuroscience, Oct. 3, 2007, 27(40):10685-10694, 2007 Society for Neuroscience.

Yasuda, S. et al., The mood stabilizers lithium and valproate selectively activate the promoter IV of brain-derived neurotrophic factor in neurons, Molecular Psychiatry, 2009, 14:51-59, 2009 Nature Publishing Group.

Shorter, E., The history of lithium therapy, Bipolar Disord, Jun. 2009, II(Suppl2):1-9.

Grandjean, E.M. et al., Lithium: Updated Human Knowledge Using an Evidence-Based Approach Part III: Clinical Safety, CNS Drugs, 2009, 23(5):397-418, 2009 Adis Data Information BV.

Seltzer, M.M. et al., Prevalence of CGG Expansions of the FMR1 Gene in a US Population-Based Sample, *Am J Med Genet B Neuropsychiatr Genet*, Jul. 2012, 159(5):1-17.

Smith, A.J. et al., Crystal Engineering of Green Tea Epigallocatechin-3-gallate (EGCg) Cocrystals and Pharmacokinetic Modulation in Rats, Molecular Pharmaceutics, Jun. 3, 2013, 10(8):2948-2961, 203 American Chemical Society.

Smith, A.J. et al., Improving Lithium Therapeutics by Crystal Engineering of Novel Ionic Cocrystals, Molecular Pharmaceutics, Nov. 5, 2013, 10(12):4728-4738, 2013 American Chemical Society.

Portis, S. et al., The role of glycogen synthase kinase-3 signaling in neurodevelopment and fragile X syndrome, Int J Physiol Pathophysiol Pharmacol, Sep. 30, 2012, 4(3):140-148.

O'Brien, W.T. et al., Validating GSK3 as an in vivo target of lithium action. *Biochem Soc Trans*, Oct. 2009, 37(pt 5):1-10.

Parker-Athill, E. et al., Flavonoids, a prenatal prophylaxis via targeting JAK2/STAT3 signaling to oppose IL-6/MIA associated autism, Journal of Neuroimmunology, Aug. 24, 2009, 217:20-27, 2009 Elsevier B.V.

Bailey, A.R. et al., Aberrant T-lymphocyte development and function in mice overexpressing human soluble amyloid precursor protein-α: implications for autism, *The FASEB Journal*, Nov. 1, 2011, 26(3):1040-1051, FASEB.

Bailey, A.R. et al., GFAP Expression and Social Deficits in Transgenic Mice Overexpressing Human sAPPα, GLIA, May 17, 2013, 61:1556-1569, 2013 Wiley Periodicals, Inc.

O'Brien, W.T. et al., Glycogen Synthase Kinase-3β Haploinsufficiency Mimics the Behavioral and Molecular Effects of Lithium, *J Neurosci*, Jul. 28, 2004, 24(30):1-21.

Arendash, G.W. et al., Behavioral Assessment of Alzheimer's Transgenic Mice Following Long-Term Aβ Vaccination: Task Specificity and Correlations between Aβ Deposition and Spatial Memory, DNA and Cell Biology, 2001, 20(11):737-744, Mary Ann Liebert, Inc.

Arendash, G.W. et al., Environmental enrichment improves cognition in aged Alzheimer's transgenic mice despite stable β-amyloid deposition, NeuroReport, Aug. 6, 2004, 15(11):1751-1754, Lippincott Williams & Wilkins.

Arendash, G.W. et al., Multi-metric behavioral comparison of APPsw and P301L models for Alzheimer's disease: linkage of poorer cognitive performance to tau pathology in forebrain, Brain Research, Feb. 21, 2004, 1012:29-41, 2004 Elsevier B.V.

Diamond, D.M. et al., Influence of Predator Stress on the Consolidation versus Retrieval of Long-Term Spatial Memory and Hippocampal Spinogenesis, *Hippocampus*, Mar. 28, 2006, 16:571-576, 2006 Wiley-Liss, Inc.

Liu, Z. et al., Lithium: A Promising Treatment for Fragile X Syndrome, ACS Chemical Neuroscience, May 11, 2014, 5:477-483, 2014 American Chemical Society.

Franklin, A.V. et al., Gycogen synthase kinase-3 inhibitors reverse deficits in long-term potentiation and cognition in Fragile X mice, *Biol Psychiatry*, Feb. 1, 2014, 75(3):1-17.

McBride, S. M.J. et al., Pharmacological Rescue of Synaptic Plasticity, Courtship Behavior, and Mushroom Body Defects in a *Drosophila* Model of Fragile X Syndrome, Neuron, Mar. 3, 2005, 45:753-764, 2005 Elsevier Inc.

Leung, H.T.T. et al., Epilepsy in four genetically determined syndromes of intellectual disability, Journal of Intellectual Disability Research, Jan. 2013, 57(1):3-20, 2011 The Authors. Journal of Intellectual Disability Research, 2011 Blackwell Publishing Ltd.

Langer, R., Polymer-Controlled Drug Delivery Systems, *Acc. Chem. Res.*, Jun. 2, 1993, 26:537-542, 1993 American Chemical Society.

Thies-Flechtner, K. et al., "Effect of Prophylactic Treatment on Suicide Risk in Patients with Major Affective Disorders", *Pharmacopsychiat.*, 1996, 29:103-107, Georg Thieme Verlag Stuttgart, New York.

Goodwin, F.K. et al., "Suicide Risk in Bipolar Disorder During Treatment with Lithium and Divalproex", *JAMA*, Sep. 17, 2003, 290(11):1467-1473, American Medical Association.

Sidman, K.R. et al., "Controlled Release of Macromolecules and Pharmaceuticals from Synthetic Polypeptides Based on Glutamic Acid", *Biopolymers*, 1983, 22:547-556, John Wiley & Sons, Inc.

Langer, R. et al., "Biocompatibility of polymeric delivery systems for macromolecules", *Journal of Biomedical Materials Research*, 1981, 15:267-277, John Wiley & Sons, Inc.

Langer, R., "Controlled release of macromolecules", *CHEMTECH*, Feb. 1982, 98-105.

Martin, E.W., "Remington's Pharmaceutical Sciences", *Journal of Pharmaceutical Sciences*, Sep. 1966, 55(9):993-994, 1965, Mack Publishing Co., Easton, Pa.

Habib, A. et al., "LISPRO mitigates ß-amyloid and associated pathologies in Alzheimer's mice", *Cell Death and Disease*, Jun. 15, 2017, 8(e2880):1-13, Nature Publishing Group.

Avrahami, L. et al., "GSK-3 inhibition: Achieving moderate efficacy with high selectivity", *Biochimica et Biophysica Acta*, 2013, 1834:1410-1414, Elsevier B.V.

* cited by examiner

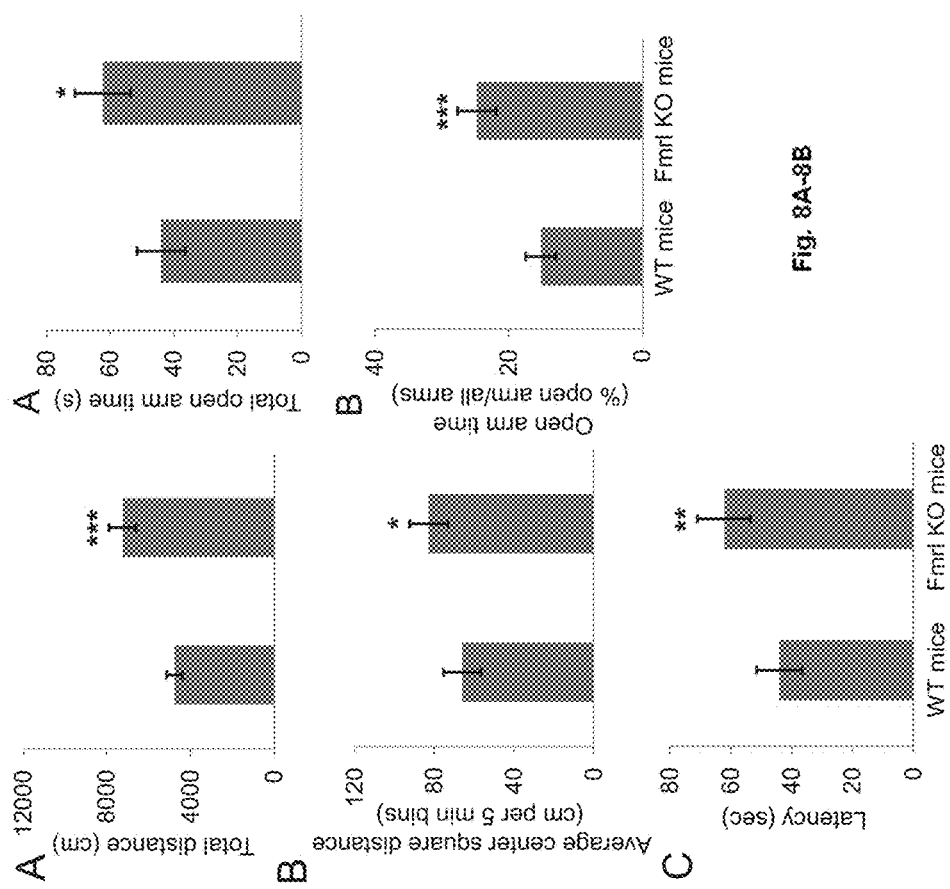

IONIC COCRYSTAL OF LITHIUM, LISPRO, FOR THE TREATMENT OF FRAGILE X SYNDROME

CROSS-REFERENCE TO A RELATED APPLICATION

This application claims the benefit of U.S. Provisional Application Ser. No. 62/291,941, filed Feb. 5, 2016, the disclosure of which is hereby incorporated by reference in its entirety, including all figures, tables and drawings.

BACKGROUND OF THE INVENTION

Lithium salts have a long history of human consumption beginning in the 1800s. In psychiatry, they have been used to treat mania and as a prophylactic for depression since the mid-20$^{th}$ century (Shorter 2009). Today, lithium salts are used as a mood stabilizer for the treatment of bipolar disorder and also, off-label, for other psychiatric indications. For example, lithium is the only drug that consistently reduces suicidality in patients with neuropsychiatric disorders (Thies-Flechtner, Muller-Oerlinghausen et al. 1996, Goodwin, Fireman et al. 2003). Despite these effective medicinal uses, current FDA approved lithium pharmaceutics (lithium carbonate and lithium citrate) are plagued with a narrow therapeutic window that requires regular blood monitoring of plasma lithium levels and blood chemistry by a clinician to mitigate adverse events. Because conventional lithium salts (carbonate and citrate) are eliminated relatively quickly, multiple administrations throughout the day are required to safely reach therapeutic plasma concentrations.

Fragile X Syndrome and Modeling in Mice—

Fragile X syndrome (IAS) is the most common cause of inherited mental retardation. It is mediated by a mutation of the first identified autism-related gene, known as fragile X mental retardation-1 (Fmr1), which encodes the fragile X mental retardation protein (FMRP), an RNA binding protein that regulates translation (1, 2). This functional loss typically occurs when there is an expansion of the CGG trinucleotide repeat in the 5' untranslated region of the Fmr1 gene (3, 4). This expansion appears as a weak, or "fragile-like", end on the X chromosome. Since FXS is an X-linked developmental disorder, its severity and incidence is higher in males than females, affecting ~1 in 4,000 males and ~1 in 7,000 females (5). Transmission of the affected. Fmr1 allele may occur to female offspring from an affected male and to both male and female offspring from affected females. Importantly, patients affected by FXS have many characteristics commonly associated with Autism Spectrum Disorders (ASDs), characterized by several physical, mental, and behavioral abnormalities, including sleep disturbances, inattentiveness, hyperactivity, impaired cognition, seizure susceptibility, developmental delays, communication impairments, and anxiety (2, 6-12).

Glycogen Synthase Kinase—

Recent studies have shown that Fmr1 KO mice express elevated levels of glycogen synthase kinase 3 (GSK3) activity. GSK3 is a serine/threonine kinase that exists in two isoforms, GSK3α and GSK3β. Regulation of GSK3 is primarily mediated by inhibitory serine-phosphorylation, specifically at Ser21 of GSK3α and Ser9 of GSK3β. The inhibitory serine-phosphorylation of GSK3 is induced by a wide variety of signaling pathways that converge on GSK3, including protein kinase A (PKA), PKB (Akt), PKC, and ribosomal S6 kinase (13). Impairments in these inhibitory pathways can lead to hyperactive GSK3, which can contribute to a number of diseases including FXS, Alzheimer's disease, diabetes and mood disorders (14-16). In addition, to be fully activated, the GSK3 isoforms must be phosphorylated at the stimulatory phosphorylation sites, specifically at Tyr279 for GSK3α and Tyr216 for GSK3β. Studies of the actions of GSK3 were accelerated by the discovery that lithium, the classical treatment for bipolar disorder, is a selective inhibitor of this kinase (17). Lithium both directly inhibits GSK3 activity and also increases the inhibitory serine-phosphorylation of this enzyme (14).

Direct evidence that GSK3 may be involved in the pathology of FXS and thus a therapeutic target is currently an important area of investigation. Preliminary evidence for this connection was obtained in studies of the regulation of GSK3 in brain regions from Find. KO mice. Adult Fmr1 KO mice have lower levels of inhibitory GSK3α (Ser21) and GSK3β (Ser9) phosphorylation in several brain regions compared to wild-type littermates (18-23,46). The impaired serine-phosphorylation of GSK3 in adult Fmr1 KO mice was corrected by acute or chronic treatment with lithium (18-24). In addition, dfmr1 mutant *Drosophila* and Fmr1 KO mice display FXS behavioral phenotypes, including hyperactivity, social and cognitive impairment, all of which is reversed by lithium (18, 21, 23, 46, 47). Several selective inhibitors of GSK3, including SB-216763, TDZD-8 and VP0.7, also reverse these behavioral deficits (18, 46), confirming that this effect of lithium is mediated by inhibition of GSK3. Most importantly, lithium has been commonly used to treat mood instability and aggression in FXS patients (7). In a recent pilot clinical trial, FXS patients treated with lithium orally for 2 months showed improvements in aggression, anxiety, mood swings, tantrums, and abnormal outbursts (25; reviewed in 15 and 45). Positive responses were observed across the age range of the study cohort, suggesting that both children and young adults with FXS can benefit from this treatment. Taken together, these results support the hypothesis that impaired inhibition of GSK3 contributes to impairments in FXS and that lithium may have therapeutic potential by increasing the inhibitory phosphorylation of this enzyme.

Dendritic Abnormalities, BDNF and Lithium—

In addition to excessive GSK3 activity and behavioral impairment, Fmr1 KO mice and patients with FXS have impairments in neuronal spine density and morphology, manifested as abnormally long, thin spines in apical dendrites of neocortical and hippocampal pyramidal neurons (26). This suggests that dendritic spines fail to fully mature in this condition. Fmr1 KO mice also exhibit impairment in hippocampal long term potentiation, indicative of impaired synaptic plasticity, which can be fully restored with administration of brain derived neurotrophic factor (BDNF; 28, 46), a potent modulator of learning and memory, synaptic plasticity and neurogenesis (27). Moreover, lithium has been reported to increase BDNF levels in cortical neurons, which can be mimicked by pharmacological inhibition of GSK (29). Although lithium has therapeutic potential for the treatment of FXS, the lithium salt formulations currently available provide a narrow therapeutic window due, in part, to their poor physicochemical properties (30, 31). In addition, lithium has numerous side-effects and the optimal effective dose of lithium for the treatment of neurodegenerative disorders without eliciting side effects is currently unknown.

BRIEF SUMMARY OF THE INVENTION

The invention provides a pharmaceutical composition comprising an ionic co-crystal (ICC) of lithium with salicylic acid and 1-proline (LISPRO). The pharmaceutical composition can further comprise an anti-inflammatory agent, for example, salicylic acid. An embodiment of the invention provides a method for treating Fragile X Syndrome (FXS) in a subject by administering to the subject a composition comprising a pharmaceutically effective amount of LISPRO.

BRIEF DESCRIPTION OF THE DRAWINGS

FIGS. 7A-7C. The hyperactive behavioral phenotypes of hurt KO mice. To establish the procedure for determining behavioral deficiency in Fmr1 KO mice, Fmr1 KO mice and WT littermates at 4 months of age were analyzed using the open field (OF), passive avoidance and elevated plus-maze behavior tests. Throughout the 30 min testing period of the OF test, the Fmr1 KO mice traveled a greater total distance (7A) as well as spending significantly more time in the central area compared with WT mice (7B). Using the passive avoidance test, Fmr1 KO mice exhibited a significantly increased latency to enter the dark chamber 24 h after training (7C). n=4 male per group.

FIGS. 8A-8B. Fmr1 KO mice display altered behavior in the elevated plus-maze. Using the elevated plus maze, Fmr1 KO mice spent significantly more total time (8A) and higher percentage of time (8B) on the open arms than did WT mice. n=4 male per group. $*p<0.05$; $p<0.01$, $*p<0.001$.

DETAILED DISCLOSURE OF THE INVENTION

FXS is caused by the expansion of a set of nucleic acid repeats in a single X chromosome gene known as Fmr1, which when fully mutated fails to express and produce a protein (FMRP) required for healthy brain development. Seltzer et al, (2012) reported that the cascade of nucleic acid repeats, which accumulate over generations and culminate in the mutation of Fmr1, is occurring with more frequency among Americans than previously believed (32). Thus, the pre-mutation of FXS is much more prevalent than previously thought, which makes finding a disease modifying therapy all the more important as there is a signal that incidence of FXS could increase in the future. Importantly, no disease modifying treatments for FXS is available. Lithium improves behavior in Fmr1 KO mice as well as in clinical trials of humans with FXS (18-25, 46).

An embodiment of the invention provides several novel ionic co-crystals (ICC) of lithium that exhibit improved oral bioavailability as well as selective uptake by the brain compared to existing treatments. In one embodiment, an ICC of lithium is LISPRO. Crystal structures of ICC are reported (34). In certain embodiments, LISPRO is used for the treatment of FXS.

Figure 1:
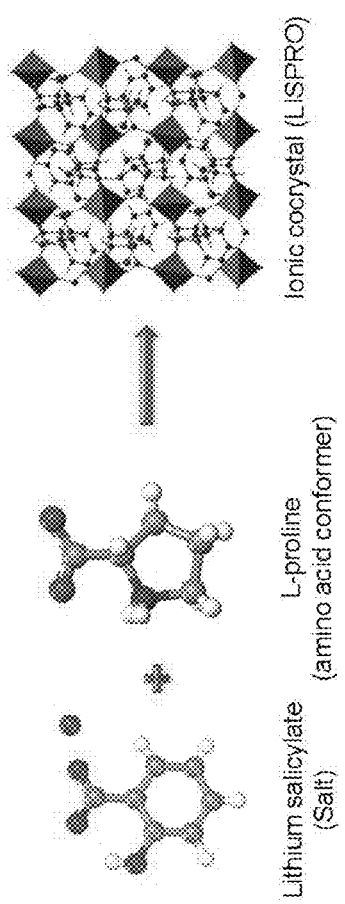
FIG. 1. LISPRO, MW 259.18. Reaction/Crystal structure. Lithium salicylate (≥98% pure, anhydrous, 1 mmol) and L-proline (≥99% pure, 1 mmol) were dissolved in 2 mL of hot deionized water. The resulting solution was maintained on a hot plate (75-90° C.) to allow slow evaporation of solvent until crystals had formed. Colorless crystals of LISPRO were collected. The purity of LISPRO was confirmed by powder X-ray diffraction, differential scanning calorimetry and atomic absorption spectrometry (AAS) (34).
Figures 2A, 2B, 2C, 2D:
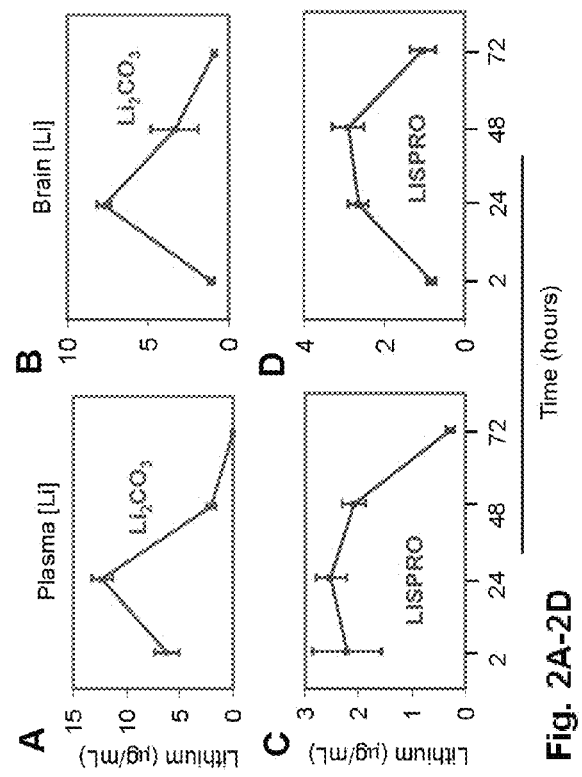
FIGS. 2A-2D. In vivo plasma and brain pharmacokinetics of LISPRO and $Li_2CO_3$. Male Sprague-Dawley rats (n=3 per formulation per time point) were dosed with 4 mEq/kg of lithium via oral gavage as LISPRO or $Li_2CO_3$. Plasma and brain lithium levels were determined at 2, 24, 48, and 72 h by AAS. (2A) $Li_2CO_3$ plasma lithium concentration, (2B) $Li_2CO_3$ brain lithium per gram of wet weight, (2C) LISPRO plasma lithium concentration and (2D) LISPRO brain lithium per gram of wet weight versus time (mean±SD). The plasma pharmacokinetics of $Li_2CO_3$ produced a sharp peak at 24 h and rapid elimination with nearly undetectable levels at 48 h (2A). This produced a concomitant spike in brain lithium levels at 24 h (2B). LISPRO produced elevated lithium plasma levels at the earliest time point (2 h) (2C). The plasma lithium levels peaked at 24 h and remained elevated at 48 h before becoming almost undetectable at 72 h. LISPRO produced steady brain levels of lithium at 24 and 48 h (2D).
Figures 3A, 3B, 3C:
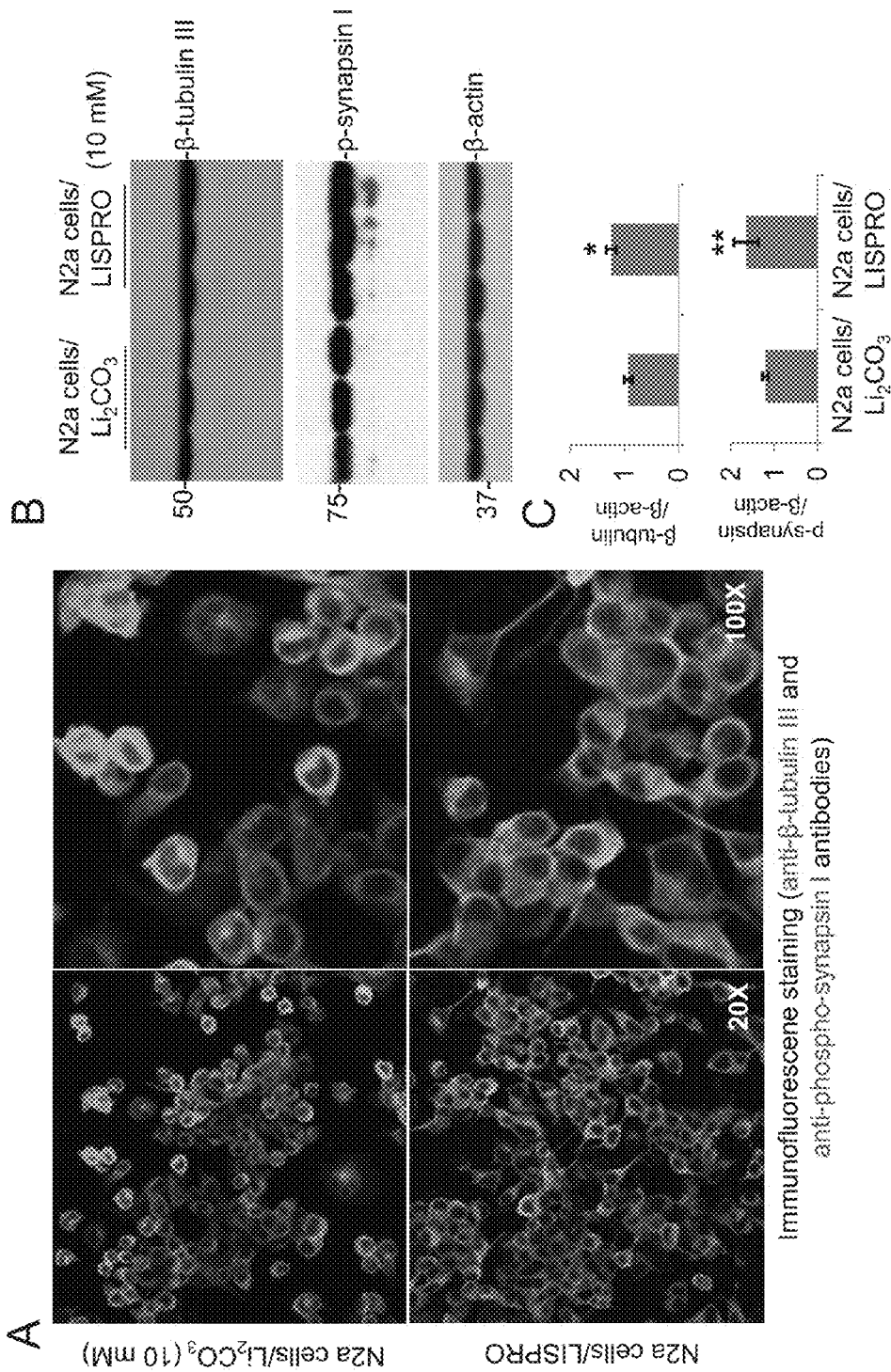
FIGS. 3A-3C, LISPRO markedly promotes neuronal cell differentiation as determined by enhanced expression of phospho-synapsin. (3A) Wild-type mouse neuroblastoma (N2a) cells were plated in 8-well slide chambers ($10^6$/well), incubated overnight, and treated with LISPRO or appropriate controls (including $Li_2CO_3$, LiCl and 1-proline, 10 mM as optimized in pilot studies, Sigma) for 24 h. These cells were then permeabilized with 0.05% Triton X-100 for 5 min, washed, and incubated with mouse anti-β-tubulin III monoclonal antibody (STEMCELL™), and rabbit anti-phospho-synapsin I ($Ser^{62}$, $Ser^{67}$) polyclonal antibody (EMD Millipore) overnight at 4° C. Alexa Fluor® 488 Goat anti-mouse IgG (green) and Alexa Fluor® 594 Donkey anti-rabbit IgG (red, Life Technologies) were used to detect β-tubulin III and phospho-synapsin I signals respectively. Confocal images were taken by Olympus Fluoview™ FV1000 laser scanning confocal microscope (Tokyo, Japan). (3B) In parallel, additional N2a cells were cultured in 6-well plates ($3 \times 10^6$/well), treated with LISPRO, $Li_2CO_3$, LiCl or 1-proline at 10 mM, lysed with cell lysis buffer, and then subjected to western blot (WB) analysis of β-tubulin III, phospho-synapsin I or β-actin. (3C) The band density ratios of β-tubulin and phospho-synapsin I (p-synapsin I) to β-actin are presented as mean±S.D. These data are representative of three independent experiments with similar results (*p<0.05;**p<0.005). There was no significant difference in β-tubulin III and phospho-synapsin I immunofluorescence and WB analysis between PBS- and $Li_2CO_3$-, LiCl- or 1-proline-treated cells (p>0.05).
Figures 4A, 4B, 4C:
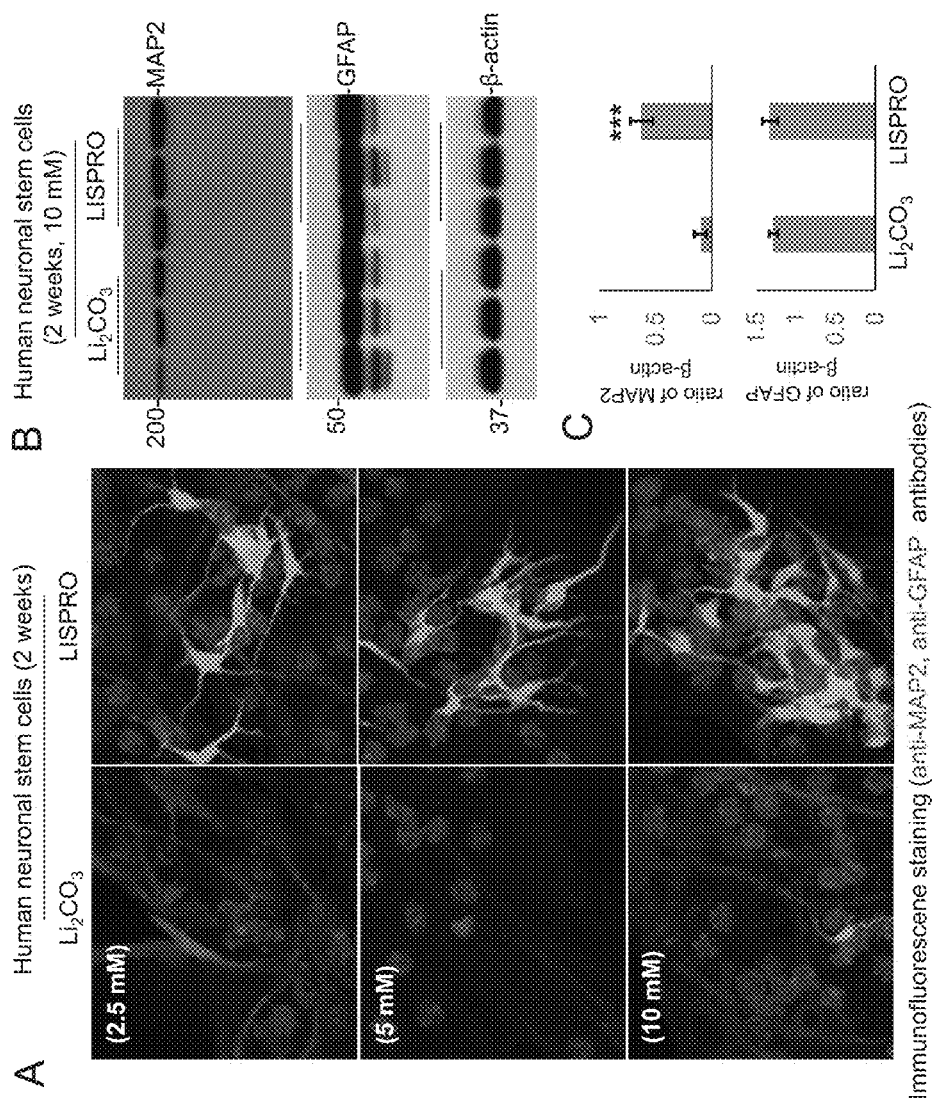
FIGS. 4A-4C, LISPRO markedly enhances human neuronal stem cell differentiation (MAP-2 expression), without enhancing gliogenesis (GFAP expression). (4A) Human neural stem cells (H9-Derived, Life technologies), cultured with StemPro® NSC SFM media, were plated in 8-well chamber slides ($10^6$/well), incubated overnight, and treated with LISPRO, $Li_2CO_3$, LiCl or 1-proline at 10 mM for 14 days. These cells were then permeabilized, washed, incubated with mouse anti-MAP2 monoclonal antibody or rabbit anti-GFAP polyclonal antibody overnight at 4° C., stained with Alexa Fluor® 488 (green) and Alexa Fluor® 594 (red), and visualized by confocal microscopy. DAPI (blue) was used to detect nuclear DNA. (4B) In parallel, additional human neuronal stem cells were cultured in 6-well plates ($3 \times 10^6$/well), treated with LISPRO, $Li_2CO_3$, LiCl or 1-proline, lysed with cell lysis buffer, and analyzed by WB. (4C) The band density ratios of MAP2 to β-actin (***p<0.001) and GFAP to β-actin (p>0.05) are presented as mean±S.D. These data are representative of two independent experiments with similar results. Note that there was no significance difference in MAP2 and GFAP immunofluorescence and WB analyses between PBS- and $Li_2CO_3$-, LiCl- or 1-proline-treated neuronal stem cells (p>0.05).
Figures 5A, 5B:
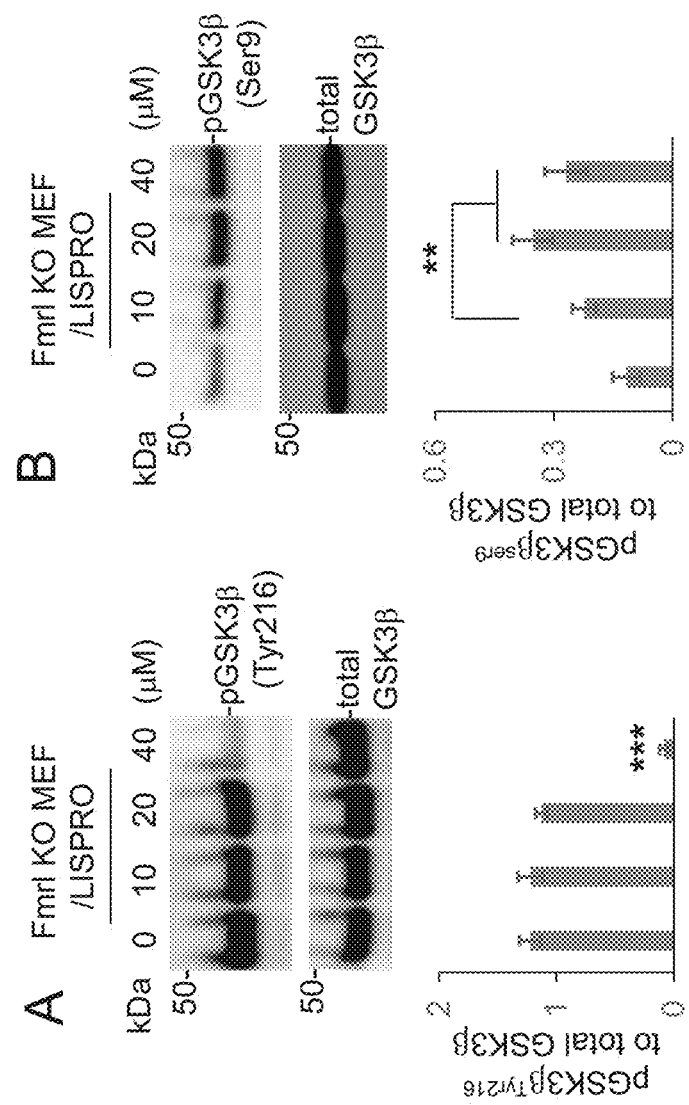
FIGS. 5A-5B. LISPRO treatment markedly reduces GSK3β (Tyr216) stimulatory phosphorylation, while enhancing GSK3β (Ser9) inhibitory phosphorylation, in Fmr1 KO mouse embryonic fibroblasts. Many neurodegenerative disorders, including FXS, have been associated with enhanced GSK activity (14-16). Fmr1 KO mouse embryonic fibroblasts (Fmr1 KO MEF) have elevated levels of stimulatory GSK3β (Tyr21.6) phosphorylation compared to wild-type MEF (both cell lines kindly provided by Dr. David Nelson, Baylor College of Medicine). Thus, whether LISPRO could reduce the abnormally elevated levels of GSK3β (Tyr216) phosphorylation, as well as enhance GSK3β (Ser9) inhibitory phosphorylation in Fmr1 KO MEF was tested. Fmr1 KO MEF were routinely cultured in 6-well plates and treated with LISPRO at 0, 10, 20, or 40 μM for 60 min. Cell lysates were then prepared and subjected to WB analysis using specific phospho-GSK3β (pGSK3β)$^{Tyr216}$, pGSK3β$^{Ser9}$ and total GSK antibodies. As shown, LISPRO decreased stimulatory pGSK3β$^{Tyr216}$ at 40 μM (5A) and increased inhibitory pGSK3β$^{Ser9}$ starting at 10 μM (5B), while leaving total GSK3β unchanged. Densitometry analysis followed by one-way ANOVA shows that LISPRO at 40 μM significantly reduced the band density ratio of pGSK3β$^{Tyr216}$ to total GSK3β (5A, lower panel), while significantly increasing the band density ratio of pGSK3β (Ser9) to total GSK3β (5B, lower panel). n=3 per group. **p<0.01; *p<0.001.
Figures 6A, 6B:
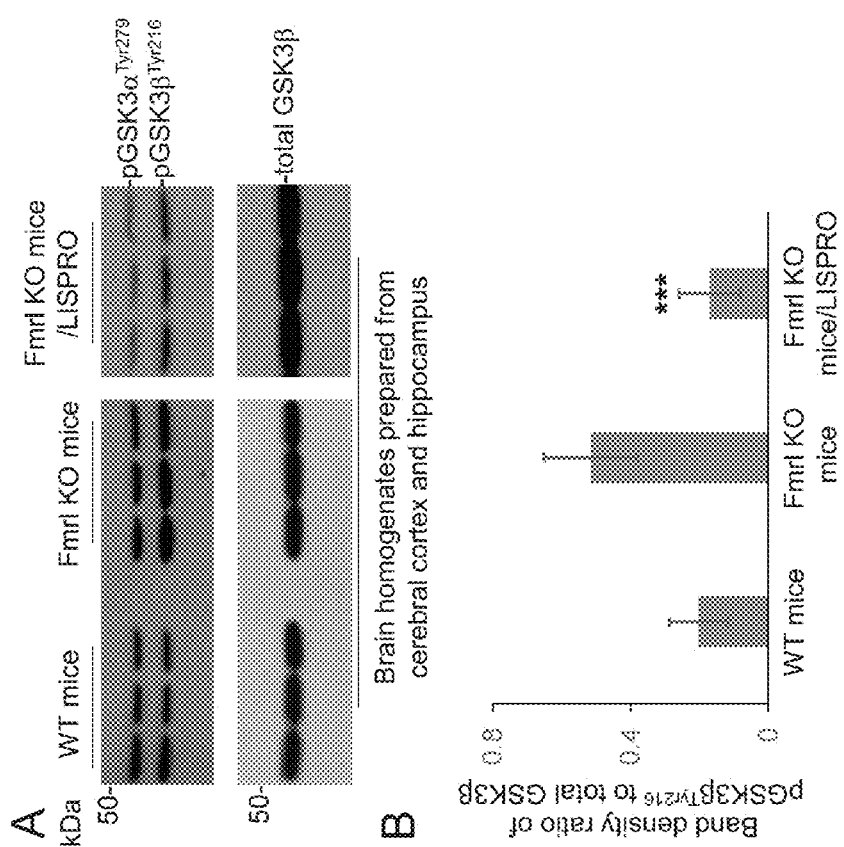
FIGS. 6A-6B, Fmr1 KO mice treated intraperitoneally with LISPRO show decreased levels of stimulatory GSK3α$^{Tyr279}$ and GSK3β$^{Tyr216}$ phosphorylation. Fmr1 KO mice (Jackson Laboratory, Fmr1$^{tm1}$Cgr/J) and wild-type littermates (C57BL/6) were treated daily with LISPRO at 28 mg/kg/day by i.p. injection (34, 35) or vehicle (PBS) for 5 days. (6A) Mouse brain homogenates were then prepared from cerebral cortex and hippocampus and analyzed by WB with specific pGSK3α$^{Tyr279}$, pGSK3β$^{Tyr216}$ and total GSK antibodies. Fmr1 KO mice expressed elevated levels of pGSK3α$^{Tyr279}$ and pGSK3β$^{Tyr216}$, while LISPRO reduced these levels, (6B) Densitometry analysis followed by one-way ANOVA shows that the band density ratio of pGSK3β$^{Tyr216}$ to total GSK3β is elevated in untreated Fmr1 KO mice compared with WT littermates and reversed to WT levels by LISPRO treatment. n=3 per group. ***p<0.001.

Pharmacokinetic and biological characterization data for LISPRO are presented herein. While the conventional lithium formulation, $Li_2CO_3$, produces a spike in plasma and brain lithium levels at 24 h with considerably lower or undetectable levels at 48 h after oral dosing, LISPRO produces nearly steady levels of lithium in plasma and brain for up to 48 h without the initial spike (FIG. 2). In addition, LISPRO exhibits improved brain bioavailability (brain/plasma ratio). Thus, LISPRO is a more controlled release formulation of lithium than conventional lithium formulations, without the potential side effects commonly associated with the initial spike. As such, LISPRO provides a safer, less expensive, and more effective treatment for psychiatric and neurodegenerative disorders, at comparably lower doses than that for traditional lithium formulations.

In one embodiment, LISPRO is administered to a patient in complex with salicylic acid, which is a common anti-inflammatory agent. Since the pathology of many neurodegenerative diseases, including FXS (48), is associated with inflammation, the formulation comprising LISPRO and salicylic acid affords anti-inflammatory effects for the treatment of FXS compared to using $Li_2CO_3$ alone.

Accordingly, an embodiment of the invention provides a pharmaceutical composition comprising LISPRO. In a further embodiment, the pharmaceutical composition comprises LISPRO and an anti-inflammatory agent. The anti-inflammatory agent can be a steroidal anti-inflammatory agent or a non-steroidal anti-inflammatory agent. In one embodiment, the anti-inflammatory agent is salicylic acid.

The subject invention provides for therapeutic or pharmaceutical compositions comprising a therapeutically effective amount of the LISPRO, either alone or in combination with an anti-inflammatory agent, and, optionally, one or more pharmaceutically acceptable carriers. Such pharmaceutical carriers can be liquids, such as water. The therapeutic composition can also comprise excipients, adjuvants, flavoring agents, etc. that facilitate processing of the active compounds into preparations that can be used pharmaceutically. Proper formulation is dependent upon the route of administration chosen. In an embodiment, the therapeutic composition and all ingredients contained therein are sterile.

The term "carrier" refers to a diluent, adjuvant, excipient, or vehicle with which the compound is administered. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the enteral mode of administration.

In one embodiment, the administration of the composition can be systemic. Oral, intravenous, intra-arterial, subcutaneous, intra-peritoneal, intra-thecal, intra-muscular, intra-ventricular, intra-nasal, transmucosal, subcutaneous, topical, rectal, and other modes of administration are all contemplated. The compositions can be designed to facilitate the subject compositions to crossing blood brain barrier.

In one embodiment, for injection, the active ingredient can be formulated in aqueous solutions, preferably in physiologically compatible buffers. For transmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. Formulations can also be prepared for use in inhalation therapy. For administration by inhalation, the composition can be delivered in the form of an aerosol spray presentation from pressurized packs or a nebulizer, with the use of a suitable propellant. The composition can also be administered via inhalation or other route as a powder.

In particular embodiments, the therapeutic composition is a sustained-release system. Suitable examples of sustained-release systems include suitable polymeric materials (such as, semi-permeable polymer matrices in the form of shaped articles, for example films, or microcapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracisternally, intraperitoneally, topically (as by powders, ointments, gels, drops or transdermal patch), or as an oral or nasal spray. Sustained-release matrices include polylactides (U.S. Pat. No. 3,773,919, EP 58,480, copolymers of L-glutamic acid and gamma-ethyl-L-glutamate (Sidman et al., Biopolymers 22:547-556, 1983, poly(2-hydroxyethyl methacrylate)); (Langer et al., J. Biomed. Mater. Res. 15:167-277, 1981; Langer, Chem. Tech. 12:98-105, 1982, ethylene vinyl acetate (Langer et al., Id.) or poly-D-(-)-3-hydroxybutyric acid (EP 133,988).

In one embodiment, implantable drug infusion devices may be used to provide patients with a constant and long-term dose or infusion of a therapeutic composition. Such device can be categorized as either active or passive.

In one embodiment, polymers can be used for ion-controlled release. Various degradable and non-degradable polymeric matrices for use in controlled drug delivery are known in the art (Langer, Accounts Chem. Res. 26:537, 1993). For example, the block copolymer, poloxamer 407, hydroxyapatite, and liposomes.

The pharmaceutical composition of the present invention may be used either alone or in combination with one or more drugs known to be effective for treating FXS. The compositions can also be formulated in combination with at least one other agent, such as stabilizing or buffer compounds, which can be administered in any sterile, biocompatible pharmaceutical carrier, including, but not limited to, saline, buffered saline, dextrose, and water. In addition to LISPRO and optionally, an anti-inflammatory agent, the compositions can contain suitable pharmaceutically acceptable carriers comprising excipients and auxiliaries that facilitate processing of the active compounds into preparations that can be used pharmaceutically. The composition may be prepared as a single-dose form using a pharmaceutically acceptable carrier or excipient or may be contained in a multiple-dose container.

A further embodiment of the invention provides a method of treating FXS in a subject by administering to the subject a pharmaceutically effective amount of LISPRO. LISPRO can be administered alone or in combination with an anti-inflammatory agent. The anti-inflammatory agent can be a steroidal anti-inflammatory agent or a non-steroidal anti-inflammatory agent. In one embodiment, the anti-inflammatory agent is salicylic acid. Steroidal and non-steroidal anti-inflammatory agents are known in the art and such embodiments are within the purview of the invention.

In certain embodiments, a pharmaceutically effective amount is administered to a subject to produce Lithium concentration in the plasma of the subject of: about 0.5 µg/ml to about 5 µg/ml, preferably, about 0.75 µg/ml to about 4 µg/ml, and more preferably, about 1 µg/ml to about 3 µg/ml, over about 2 hours to about 3 days, particularly, over about 2 hours to about 2 days.

In certain embodiments, a pharmaceutically effective amount is administered to a subject to produce Lithium concentration in the brain of the subject of: about 0 µg/ml to about 5 µg/ml, preferably, between about 0.75 µg/ml to about 4 µg/ml, and more preferably, about 1 µg/ml to about 3 µg/ml, over about 2 hours to about 4 days, particularly, over about 2 hours to about 3 days.

In certain embodiments, LISPRO is administered daily to a subject at about 10 mg/kg to 50 mg/kg, preferably, at about 15 mg/kg to about 45 mg/kg, more preferably at about 20 mg/kg to about 40 mg/kg, and even more preferably, at about 25 mg/kg to about 35 mg/kg. In a particular embodiment, LISPRO is administered daily to a subject at about 30 mg/kg/day.

In further embodiments, dose of LISPRO equivalent to several days is administered based on a daily dose of about 10 mg/kg to about 50 mg/kg, preferably, about 20 mg/kg to about 40 mg/kg, and even more preferably, about 25 mg/kg to about 35 mg/kg.

In a particular embodiment, dose of LISPRO equivalent to several days is administered based on a daily dose of about 30 mg/kg. For example, a dose equivalent to 5 days is administered at once at about 150 mg/kg.

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", include the phrases "consisting essentially of", "consists essentially of", "consisting", and "consists".

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e. the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients or doses administered to a subject, the terms "about" indicates that the relevant parameter is with a variation (error range) of 0-10% around the value (X±10%).

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional medium or agent is incompatible with the active agents described herein, its use in the compositions of the invention is contemplated.

When ranges are used herein, such as for dose ranges, combinations and sub-combinations of ranges (e.g., sub-ranges within the disclosed range), specific embodiments therein are intended to be explicitly included.

"Treatment" or "treating" (and grammatical variants of these terms), as used herein, are used interchangeably. These terms refer to an approach for obtaining beneficial or desired results including but not limited to therapeutic benefit. A therapeutic benefit is achieved with the eradication or amelioration of one or more of the physiological symptoms associated with FXS such that an improvement is observed in the patient, notwithstanding that the patient may still be afflicted with FXS.

The term "effective amount" or "therapeutically effective amount" refers to that amount of active agents described herein that is sufficient to effect the intended application including but not limited to FXS treatment. The therapeutically effective amount may vary depending upon the intended application and the subject and disease condition being treated, e.g., the weight and age of the subject, the severity of FXS, and the manner of administration. The specific dose will vary depending on the particular agents chosen, the dosing regimen to be followed, whether it is administered in combination with other compounds, timing of administration, the tissue to which it is administered, and the physical delivery system in which it is carried.

"Subject" refers to an animal, such as a mammal, for example a human.

All patents, patent applications, provisional applications, and publications referred to or cited herein are incorporated by reference in their entirety, including all figures and tables, to the extent they are not inconsistent with the explicit teachings of this specification.

REFERENCES

1. Bear M F, Huber K M, Warren S T (2004). The mGluR theory of fragile X mental retardation. Trends Neurosci 27: 370-7.
2. Koukoui S D, Chaudhuri A (2007). Neuroanatomical, molecular genetic, and behavioral correlates of fragile X syndrome. Brain Res Rev 53: 27-38.
3. Crawford D C, Zhang F, Wilson B, Warren S T, Sherman S L (2000), Fragile X CGG repeat structures among African-Americans: identification of a novel factor responsible for repeat instability. Hum Mol Genet 9(12): 1759-69.
4. Garber K B, Visootsak J, Warren S T (2008). Fragile X syndrome. Eur J Hum Genet 16(6):666-72
5. Crawford D C, Acuna J M, Sherman S L (2001). FMR1 and the fragile X syndrome: Human genome epidemiology review. Genet Med 3: 359-371.
6. Belmonte M K, Bourgeron T (2006). Fragile X syndrome and autism at the intersection of genetic and neural networks. Nat Neurosci 9: 1221-5.
7. Hagerman R J, Ono M Y, Hagerman P J (2005). Recent advances in fragile X: a model for autism and neurodegeneration. Curr Opin Psychiatry 18: 490-6.
8. Hatton D D, Sideris J, Skinner M, Mankowski J, Bailey D B, Jr., Roberts J, Mirrett P (2006). Autistic behavior in children with fragile X syndrome: prevalence, stability, and the impact of FMRP. Am J Med Genet A 140A: 1804-13.
9. Kau A S, Tierney F, Bukelis I, Stump M H, Kates W R, Trescher W H, Kaufmann W E (2004). Social behavior profile in young males with fragile X syndrome: characteristics and specificity. Am J Med Genet A 126A: 9-17.
10. Loesch D Z, Bui Q M, Dissanayake C, Clifford S, Gould E, Bulhak-Paterson D, Tassone F, Taylor A K, Hessl D, Hagerman R, Huggins R M (2007). Molecular and cognitive predictors of the continuum of autistic behaviours in fragile X. Neurosci Biobehav Rev 31: 315-26.
11. Moy S S, Nadler J J (2008). Advances in behavioral genetics: mouse models of autism. Mol Psychiatry 13: 4-26.
12. Sullivan K, Hatton D, Hammer J, Sideris J, Hooper S, Ornstein P, Bailey D, Jr. (2006) ADHD symptoms in children with FXS. Am J Med Genet A 140: 2275-88,
13. Doble B W, Woodgett J R (2003), GSK-3: tricks of the trade for a multi-tasking kinase. J Cell Sci 116(Pt 7):1175-86.
14. Jope R S, Johnson G V (2004). The glamour and gloom of glycogen synthase kinase-3. Trends Biochem Sci 29: 95-102.
15. Mines M A, Jope R S (2011). Glycogen synthase kinase-3: a promising therapeutic target for fragile x syndrome. Front Mol Neurosci 4: 35.
16. Mines M A, Yuskaitis C J, King M K, Beurel E, Jope R S (2010). GSK3 influences social preference and anxiety-related behaviors during social interaction in a mouse model of fragile X syndrome and autism. PloS One 5: e9706.
17. Klein P S, Melton D A (1996). A molecular mechanism for the effect of lithium on development. Proc Natl Acad Sci USA 93: 8455-9.
18. Min W W, Yuskaitis C J, Yan Q, Sikorski C, Chen S, Jope R S, Bauchwitz R P (2009), Elevated glycogen synthase kinase-3 activity in Fragile X mice: key metabolic regulator with evidence for treatment potential. Neuropharmacology 56: 463-72.
19. Yuskaitis C J, Beurel E, Jope R S (2010a). Evidence of reactive astrocytes but not peripheral immune system activation in a mouse model of Fragile X syndrome. Biochim Biophys Acta 1802: 1006-12.
20. Yuskaitis C J, Jope R S (2009). Glycogen synthase kinase-3 regulates microglial migration, inflammation, and inflammation-induced neurotoxicity. Cell Signal 21: 264-73.
21. Yuskaitis C J, Mines M A, King M K, Sweatt J D, Miller C A, Jope R S (2010b). Lithium ameliorates altered glycogen synthase kinase-3 and behavior in a mouse model of Fragile X syndrome. Biochem Pharmacol 79: 632-646.
22. Liu Z-H, Smith C B (2009). Dissociation of social and nonsocial anxiety in a mouse model of fragile X syndrome. Neurosci Lett 454: 62-66.
23. Liu Z H, Chuang D M, Smith C B (2011). Lithium ameliorates phenotypic deficits in a mouse model of fragile X syndrome. Int J Neuropsychopharmacol 14: 618-30.
24. Liu Z H, Huang T, Smith C B (2012). Lithium reverses increased rates of cerebral protein synthesis in a mouse model of fragile X syndrome. Neurobiol Dis 45: 1145-52.
25. Berry-Kravis E, Sumis A, Hervey C, Nelson M, Porges S W, Weng N, Weiler I J, Greenough W T (2008). Open-label treatment trial of lithium to target the underlying defect in fragile X syndrome. J Dev Behav Pediatr 29: 293-302.
26. Comery T A, Harris J B, Willems P J, Oostra B A, Irwin S A, Weiler I J, Greenough W T (1997), Abnormal dendritic spines in fragile X knock-out mice: maturation and pruning deficits. Proc Natl Acad Sci USA 94:5401-5404.
27. Waterhouse E G, Xu B (2009). New insights into the role of brain-derived neurotrophic factor in synaptic plasticity Mol Cell Neurosci 42(2):81-9
28. Lauterborn J C, Rex C S, Kramár E, Chen L Y, Pandyarajan V, Lynch G, Gall C M (2007). Brain-derived neurotrophic factor rescues synaptic plasticity in a mouse model of fragile X syndrome. J Neurosci 27(40):10685-94.
29. Yasuda S, Liang M H, Marinova Z, Yahyavi A, Chuang D M (2009). The mood stabilizers lithium and valproate selectively activate the promoter IV of brain-derived neurotrophic factor in neurons. Mol Psychiatry. 14(1):51-9.
30. Shorter E (2009). The history of lithium therapy. Bipolar Disord Suppl 2:4-9.
31. Grandjean E M, Aubry J M (2009). Lithium: updated human knowledge using an evidence-based approach: part III: clinical safety, CNS Drugs 23(5):397-418. Review.
32. Seltzer M M, Baker M W, Hong J, Maenner M, Greenberg J, Mandel D (2012). Prevalence of CCG expansions of the FMR1 gene in a US population-based sample. Am J Med Genet 159B: 589-597.

33. Smith A J, Kavuru P. Arora K K, Kesani S. Tan J, Zaworotko M J, Shytle R D (2013). Crystal Engineering of Green Tea Epigallocatechin-3-gallate (EGCg) Cocrystals and Pharmacokinetic Modulation in Rats. Mol Pharm 10(8):2948-61.
34. Smith A J, Kim S R, Duggirala N K, Jin J, Wojtas L, Ehrhart J, Giunta B, Tan J, Zaworotko M J, Shytle R D (2013). Improving lithium therapeutics by crystal engineering of novel ionic cocrystals. Mol Pharm 10(12): 4728-38.
35. Portis S, Giunta B, Obregon D, Tan J (2012). The role of glycogen synthase kinase-3 signaling in neurodevelopment and fragile X syndrome int J Physiol Pathophysiol Pharmacol 4(3): 140-8.
36. O'Brien W T, Klein P S (2009). Validating GSK3 as an in vivo target of lithium action. Biochem Soc Trans 37: 1133-8.
37. Parker-Athill E, Luo D, Bailey A, Giunta B, Tian J, Shytle R D, Murphy T, Legradi. G, Tan J (2009). Flavonoids, a prenatal prophylaxis via targeting JAK2/STAT3 signaling to oppose IL-6/MIA associated autism. J Neuroimmunol 217(1-2):20-7.
38. Bailey A R, Hou H, Obregon D F, Tian J, Zhu Y, Zou Q, Nikolic W V, Bengtson M, Mori T, Murphy T, Tan J (2012). Aberrant T-lymphocyte development and function in mice overexpressing human soluble amyloid precursor protein-α: implications for autism. FASEB J 26(3): 1040-51.
39. Bailey A R, Hou H, Song M, Obregon D F, Portis S, Barger S, Shytle D, Stock S, Mori T, Sanberg P R, Murphy T, Tan J (2013). GFAP expression and social deficits in transgenic mice overexpressing human sAPPα. Glia 61:1556-69.
40. O'Brien W T, Harper A D, Jove F, Woodgett J R, Maretto S, Piccolo S, Klein P S. (2004). Glycogen synthase kinase-3beta haploinsufficiency mimics the behavioral and molecular effects of lithium. J Neurosci. 24:6791-8.
41. Arendash G W, Gordon M N, Diamond D M, Austin L A, Hatcher J M, Jantzen P, DiCarlo G, Wilcock D, Morgan D. (2001). Behavioral assessment of Alzheimer's transgenic mice following long-term Abeta vaccination: task specificity and correlations between Abeta deposition and spatial memory. DNA Cell Biol. 20(11):737-44.
42. Arendash G W, Garcia M F, Costa D A, Cracchiolo J R, Wefes I M, Potter H (2004). Environmental enrichment improves cognition in aged Alzheimer's transgenic mice despite stable beta-amyloid deposition. Neuroreport. 15(11):1751-4.
43. Arendash G W, Lewis J, Leighty R E, McGowan E, Cracchiolo J R, Hutton M, Garcia M F (2004). Multimetric behavioral comparison of APPsw and P301L models for Alzheimer's disease: linkage of poorer cognitive performance to tau pathology in forebrain. Brain Res. 1012(1-2):29-41.
44. Diamond D M, Campbell A M, Park C R, Woodson J C, Conrad C D, Bachstetter A D, Mervis R F (2006) Influence of predator stress on the consolidation versus retrieval of long-term spatial memory and hippocampal spinogenesis. Hippocampus 16:571-6.
45. Liu Z, Smith C B (2014). Lithium: a promising treatment for fragile X syndrome. ACS Neurosci 4:477-483.
46. Franklin A V, King M K, Palomo V, Martinez A, McMahon L L, Jope R S (2014). Gycogen synthase kinase-3 inhibitors reverse deficits in long-term potentiation and cognition in fragile X mice. Biol Psychiatry 75:198-206.
47. McBride, S. M., Choi, C. H., Wang, Y., Liebelt, D., Braunstein, E., Ferreiro, D., Sehgal, A., Siwicki, K. K., Dockendortf, T. C., Nguyen, H. T., McDonald, T. V., and Jongens, T. A. (2005). Pharmacological rescue of synaptic plasticity, courtship behavior, and mushroom body defects in a *Drosophila* model of fragile X syndrome. Neuron. 45, 753-764.
48. Leung H T, Ring H. (2013). Epilepsy in four genetically determined syndromes of intellectual disability. J Intellect Disabil Res 57:3-20.

We claim:

1. A method for treating Fragile X Syndrome (FXS) in a subject in need thereof, the method comprising orally administering to the subject a composition comprising a pharmaceutically effective amount of an ionic co-crystal of lithium with salicylic acid and 1-praline (LISPRO) for at least two months, wherein the pharmaceutically effective amount is 45 mg/kg/day to 50 mg/kg/day.

2. The method of claim 1, wherein the composition further comprises an anti-inflammatory agent.

3. The method of claim 2, wherein the anti-inflammatory agent a steroidal anti-inflammatory agent or a non-steroidal anti-inflammatory agent.

4. The method of claim 1, wherein the pharmaceutically effective amount of LISPRO produces lithium concentration in the plasma of the subject over about 2 hours to about 3 days at about 0.5 µg/ml to about 5 µg/ml.

5. The method of claim 1, wherein the pharmaceutically effective amount of LISPRO produces lithium concentration in the brain of the subject over about 2 hours to about 3 days at about 0.5 µg/ml to about 5 µg/ml.

6. The method of claim 1, wherein LISPRO is administered daily to a subject at about 45 mg/kg.

7. The method of claim 1, wherein LISPRO is administered daily to a subject at about 50 mg/kg.

8. The method of claim 1, wherein the pharmaceutically effective amount of LISPRO produces lithium concentration in the plasma of the subject over about 2 hours to about 3 days at about 0.75 µg/ml to about 4 µg/ml.

9. The method of claim 1, wherein the pharmaceutically effective amount of LISPRO produces lithium concentration in the plasma of the subject over about 2 hours to about 3 days at about 1 µg/ml to about 3 µg/ml.

10. The method of claim 1, wherein the pharmaceutically effective amount of LISPRO produces lithium concentration in the brain of the subject over about 2 hours to about 3 days at about 0.75 µg/ml to about 4 µg/ml.

11. The method of claim 1, wherein the pharmaceutically effective amount of LISPRO produces lithium concentration in the brain of the subject over about 2 hours to about 3 days at about 1 µg/ml to about 3 µg/ml.

12. The method of claim 1, comprising administering LISPRO to the subject for two months.

* * * * *

UNITED STATES PATENT AND TRADEMARK OFFICE
CERTIFICATE OF CORRECTION

PATENT NO. : 10,098,909 B2
APPLICATION NO. : 15/425367
DATED : October 16, 2018
INVENTOR(S) : Jun Tan and Roland Douglas Shytle Page 1 of 2

It is certified that error appears in the above-identified patent and that said Letters Patent is hereby corrected as shown below:

In the Specification

Column 1,
Line 34, "(IAS)" should read --(FXS)--.
Line 46, "affected. Fmr1" should read --affected Fmr1--.

Column 2,
Line 14, "Find. KO mice" should read --Fmr1 KO mice--.

Column 3,
Lines 9-10, "BRIEF DESCRIPTION OF THE DRAWINGS" should read --BRIEF DESCRIPTION OF THE DRAWINGS
The patent or application file contains at least one drawing executed in color. Copies of this patent or patent application publication with color drawing(s) will be provided by the Office upon request and payment of the necessary fee.--.

Column 4,
Line 32, "GSK3β (Tyr21.6)" should read --GSK3β (Tyr216)--.
Line 51, "**p<0.01; *p<0.001" should read --$p < 0.01$; *$p < 0.001$--.

Column 5,
Line 2, "hurt KO mice" should read --Fmr1 KO mice--.

Column 6,
Line 61, "EP 58,480" should read --EP 58,481--.

Column 8,
Line 20, "i.e. the limitations" should read --i.e., the limitations--.

Signed and Sealed this
Fourteenth Day of May, 2019

Andrei Iancu
*Director of the United States Patent and Trademark Office*

Column 9,
Line 42, "Tierney F," should read --Tierney E,--.

Column 10,
Line 65, "of CCG expansions" should read --of CGG expansions--.

Column 12,
Line 7, "Dockendortf, T. C." should read --Dockendorff, T. C.--.

In the Claims

Column 12,
Line 22 (Claim 1), "1-praline (LISPRO)" should read --1-proline (LISPRO)--.